(12) United States Patent
Marks et al.

(10) Patent No.: US 7,450,243 B2
(45) Date of Patent: Nov. 11, 2008

(54) VOLUMETRIC ENDOSCOPIC COHERENCE MICROSCOPY USING A COHERENT FIBER BUNDLE

(75) Inventors: Daniel L. Marks, Urbana, IL (US); Stephen A. Boppart, Champaign, IL (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 2 days.

(21) Appl. No.: 11/656,892

(22) Filed: Jan. 23, 2007

(65) Prior Publication Data

US 2008/0007733 A1    Jan. 10, 2008

(51) Int. Cl.
*G01B 9/02* (2006.01)

(52) U.S. Cl. ........................... 356/479; 356/497
(58) Field of Classification Search .............. 356/497, 356/479
See application file for complete search history.

(56) References Cited

U.S. PATENT DOCUMENTS

| | | | |
|---|---|---|---|
| 5,493,109 A * | 2/1996 | Wei et al. | 250/201.3 |
| 5,555,087 A * | 9/1996 | Miyagawa et al. | 356/485 |
| 6,011,624 A * | 1/2000 | de Groot | 356/511 |
| 6,456,769 B1 | 9/2002 | Furusawa | 385/117 |
| 2006/0056784 A1 | 3/2006 | Hauger et al. | 385/115 |

FOREIGN PATENT DOCUMENTS

DE    103 51 319    6/2005

OTHER PUBLICATIONS

Salathé, R.P. "Coupled-Mode Propagation In Multicore Fibers Characterized by Optical Low-Coherence Reflectometry," *Optics Letters*, vol. 21, No. 13, pp. 1006-1008, Jul. 1, 1996.

Pyhtila, John W., et al. "Fourier-Domain Angle-Resolved Low Coherence Interfeerometry Through an Endoscopic Fiber Bundle for Light-Scattering Spectroscopy," *Optics Letters*, vol. 31, No. 6, pp. 772-774, Mar. 15, 2006.

Göbel, Werner, et al. "Miniaturized Two-Photon Microscope Based on a Flexible Coherent Fiber Bundle and a Gradient-Index Lens Objective," *Optics Letters*, vol. 29, No. 21, pp. 2521-2523, Nov. 1, 2004.

Casaubieilh, P., et al. "Optical Fibre Coherence Tomography Based on Fizeau Interferometer Configurations," *Proc. of SPIE*, vol. 5486, pp. 112-122, 2004.

Xie, Tuqiang "Fiber-Optic-Bundle-Based Optical Coherence Tomography," *Optics Letters*, vol. 30, No. 14, pp. 1803-1805, Jul. 15, 2005.

(Continued)

*Primary Examiner*—Tarifur Chowdhury
*Assistant Examiner*—Jonathon D Cook
(74) *Attorney, Agent, or Firm*—Bromberg & Sunstein LLP

(57) ABSTRACT

Methods for employing coherent bundles of optical fibers, whether single- or multi-mode, for optical coherence tomography or optical coherence microscopy. Either a substantially monochromatic source or a broadband source is spatially decohered and/or spatially filtered prior to coupling into the fiber bundle for illumination of a sample. A scatter signal from features disposed beneath the surface of the sample is interfered with a reference signal derived, at either end of the fiber bundle, from the identical source of illumination.

9 Claims, 5 Drawing Sheets

OTHER PUBLICATIONS

Ford, H.D., et al. "Full-Field Optical Coherence Tomography Using a Fibre Imaging Bundle," *Proc. of SPIE*, vol. 6079, Feb. 20, 2006.

Sarantavgas, G., et al. "Fizeau-Based Optical Coherence Tomography (OCT) Using a Fibre Imaging Bundle," *Photonics and Imaging in Biology and Medicine II*, No. 13.45, Sep. 5, 2006.

Ford, H.D., et al. "Full-Field Optical Coherence Tomography Using a Fibre Imaging Bundle," *Proceedings of SPIE*, vol. 6079, Feb. 20, 2006, (abstract only).

Ford, H.D., et al. "Full-Field Optical Coherence Tomography," *Proceedings of SPIE*, vol. 5858, Aug. 18, 2005, (abstract only).

Ford et al. "*Full-field optical coherence tomography using a fibre imaging bundle*", Proc. Of SPIE, vol. 6079, 60791H-1-H9, Jan. 1, 2006.

\* cited by examiner

VOLUMETRIC ENDOSCOPIC COHERENCE MICROSCOPY USING A COHERENT FIBER BUNDLE

TECHNICAL FIELD AND BACKGROUND ART

The present invention pertains to coherence microscope performed through optical fiber bundles.

Coherent optical fiber bundles that preserve the relative ordering of fibers at their respective ends are commonly used for video imaging of internal structures during internal exploration and surgery. Such means enable a physician or surgeon to see the surface of internal structures using visible light by means of a video camera coupled to the fiber bundle.

A coherent fiber bundle is a bundle of optical fibers that are arranged such that they remain parallel to each other the length of the bundle, in such a way that the nearest neighbor fibers of a particular fiber on one end of the bundle are also the neighbors on the other end. Each of the fibers in the bundle is a waveguide that conducts light from one end of the fiber to the other. The fiber typically consists of a high refractive index core, and a low refractive index cladding, and the light is confined to the core by total internal reflection. By focusing an image onto one end of the bundle, various points on the image are conducted through their respective fibers to the other end of the bundle. Because the bundle is "coherent," these points of the image emerge from the bundle in the same relative positions as they were on the incident end. The image emerging from the bundle can be further imaged onto a sensor, where it can be displayed on a television screen for visualization, for example. This is the basis for a typical fiber bundle endoscope.

FIG. 1 is a simplified schematic of an endoscope 100 as employed in the current art. A light source 102, such as a halogen light bulb, produces white light 106, which is used to illuminate the object being studied. This white light is imaged into the proximal end of a fiber bundle 108 using a lens 110 and is conducted to the object through the bundle. The light is carried in the cores 112 (shaded, in FIG. 1) of each fiber in the bundle, thus the light carried in each core remains largely separated for the length of the bundle. The illumination emerges from the distal end of the bundle and is focused by a exit optics 114 (such as second lens 114) onto the object 104. The light scatters off of the object and is recollected by exit optics 114 back into bundle 108. Part of the scattered field is coupled back into the cores 112 in the bundle, where the image is conducted from the distal back to the proximal end of the bundle. The separation between the cores keeps the light from the cores from mixing together, at least substantially, so that each core conducts essentially one picture element of the resulting image. The lens 110 then focuses the light emerging from the cores of the bundle, via a beamsplitter 118, onto a sensor 116, where pixels on the sensor detect the light from the cores.

While the fiber bundle is depicted schematically in FIG. 1 as a short rod, in reality it is typically long and flexible, although rigid designs also exist. The typical diameter of a bundle is from 0.5-5.0 mm, and the length is 10 cm or longer, up to several meters. The fiber bundle can be threaded through internal luminal structures such as within the vascular system and the gastrointestinal, urinary, or respiratory tracts. These bundles are also used to visualize regions beneath organs that a rigid endoscope would be unable to reach. A bundle can contain from several hundred to 100,000 individual fibers, so the image can be quite detailed. The fiber bundle can be integrated into a catheter with surgical instruments, so that image-guided surgery is commonplace with fiber bundles. Fiber bundles are made of durable silica or plastics and therefore can tolerate tight bends without breaking.

It is, however, desirable to visualize not only the readily imaged surface but also the subsurface structure (to, say, 1-2 mm depth) of internal tissues for various reasons, including detecting cancers in epithelial tissues (which form 85% of diagnosed cancers). Unfortunately, visible light video imaging is unsuitable for this, because of the very shallow penetration of visible light into epithelial tissue. For this reason, researchers have attempted to adapt Optical Coherence Tomography (OCT) and other coherence microscopies for use with internal imaging techniques that employ coherent fiber bundles. Unfortunately, however, coherent fiber bundles have proven unsuitable for coherence imaging, mostly because fiber bundle filaments are typically multimode waveguides which scramble the coherence signal, leak light between the filaments, and induce modal dispersion.

In OCT and optical coherence microscopy (OCM), as typically practiced, an object is illuminated with a focused beam of polychromatic light. By measuring the interferometric cross-correlation between the light backscattered from the object (the signal beam), and a reference beam, the time delay to various scattering features in the object may be inferred. In optical coherence domain reflectometry (OCDR), the relative time delay between the reference and signal beams is varied to measure the cross-correlation. In optical frequency domain reflectometry (OFDR), the frequency of the illumination is varied and the intensity of the interference is measured. A single beam can be scanned transversally to scan through an entire volume to create a 3-D image of the volume.

In conventional OCT or OCM, a single focused beam is scanned through the object to create the three-dimensional image. Unfortunately, this is not suitable for imaging with a fiber bundle. Because the fiber bundle consists of discrete imaging channels rather than a continuous space, the beam cannot be scanned to any arbitrary location in space and be confined in a fiber. This presents problems for conventional beam scanning apparatus because it is designed to scan the beam continuously over the object, usually in a raster-like pattern. Most of the time, the beam will not illuminate the core of a fiber and no useful signal will be recorded. To avoid having to scan the beam in a complicated and error prone pattern which would successively illuminate each fiber core, it is desirable that scanning the beam be avoided altogether.

SUMMARY OF THE INVENTION

In accordance with preferred embodiments of the present invention, methods and apparatus are provided for coherence microscopy through a fiber bundle.

In accordance with a preferred method, the following steps are performed:

a. illuminating a sample with light via an optical fiber bundle;

b. reducing the spatial coherence of the light prior to coupling the light into the fiber bundle;

c. collecting light scattered by features beneath the surface of the sample;

d. coupling the scattered light into a distal end of the fiber bundle; and e. interfering the illuminating light and the scattered light to derive an image of the features beneath the surface.

The method may also have a step of spatially filtering the light prior to coupling the light into the fiber bundle.

In accordance with an alternate embodiment of the invention, a method may be provided that has steps of:

a. illuminating a surface with light via an optical fiber bundle;

b. spatially filtering the light prior to coupling the light into the fiber bundle;

c. collecting light scattered by features beneath the surface of the sample;

d. coupling the scattered light into a distal end of the fiber bundle; and e. interfering the illuminating light and the scattered light to derive an image of the features beneath the surface.

In any of the foregoing methods, other aspects of the invention may include the use of a substantially monochromatic source of light, including infrared light, that is characterized by an instantaneous wavelength that is scanned over time, and may also include the use of a Fizeau interferometer disposed substantially at the distal end of the fiber bundle. The Fizeau interferometer includes an optical plate interposed between the distal end of the fiber bundle and the surface of the sample.

In accordance with other embodiments of the invention, the step of reducing the spatial coherence may include applying a mode scrambler to the illuminating light, and may include interposing a diffusing plate in the light path prior to coupling the illuminating light into the proximal end of the fiber bundle. There may also be a further step of imaging the surface of the sample in visible light, concurrently with performing optical coherence microscopy and through the same fiber bundle.

In accordance with other aspects of the invention, an apparatus is provided for performing optical coherence microscopy. The apparatus has an optical fiber bundle and a source of spatially substantially coherent light for providing illumination of a sample through the fiber bundle. A mode scrambler is interposed between the source of coherent light and the optical fiber bundle, and exit optics couple light from the optical fiber bundle onto a surface of a sample and for collecting light scattered by features beneath the surface of the sample> Finally, the apparatus has an interferometer for comparing the phase of light scattered by features beneath the surface of the sample with a reference derived from the identical source of spatially substantially coherent light. A spatial filter may also be interposed between the source of coherent light and the optical fiber bundle.

In yet other embodiments of the invention, an apparatus is provided having an optical fiber bundle and a source of substantially spatially coherent light for providing illumination of a sample through the fiber bundle. This apparatus has a spatial filter interposed between the source of coherent light and the optical fiber bundle, exit optics for coupling light from the optical fiber bundle onto a surface of the sample and for collecting light scattered by features beneath the surface of the sample, and an interferometer for comparing the phase of light scattered by features beneath the surface of the sample with a reference derived from the identical source of substantially spatially coherent light.

In any of the foregoing embodiments of the invention, the source of substantially spatially coherent light includes a substantially monochromatic source characterized by an instantaneous wavelength, possibly in the infrared, or, more particularly, in the near infrared, that is varied over time. The interfeorometer may include a Fizeau interferometer disposed substantially at the distal end of the fiber bundle, and, more specifically, an optical plate interposed between the distal end of the fiber bundle and the surface of the sample.

BRIEF DESCRIPTION OF THE DRAWINGS

The foregoing features of the invention will be more readily understood by reference to the following detailed description, taken with reference to the accompanying drawings, in which.

DETAILED DESCRIPTION OF SPECIFIC EMBODIMENTS

Figure 1:
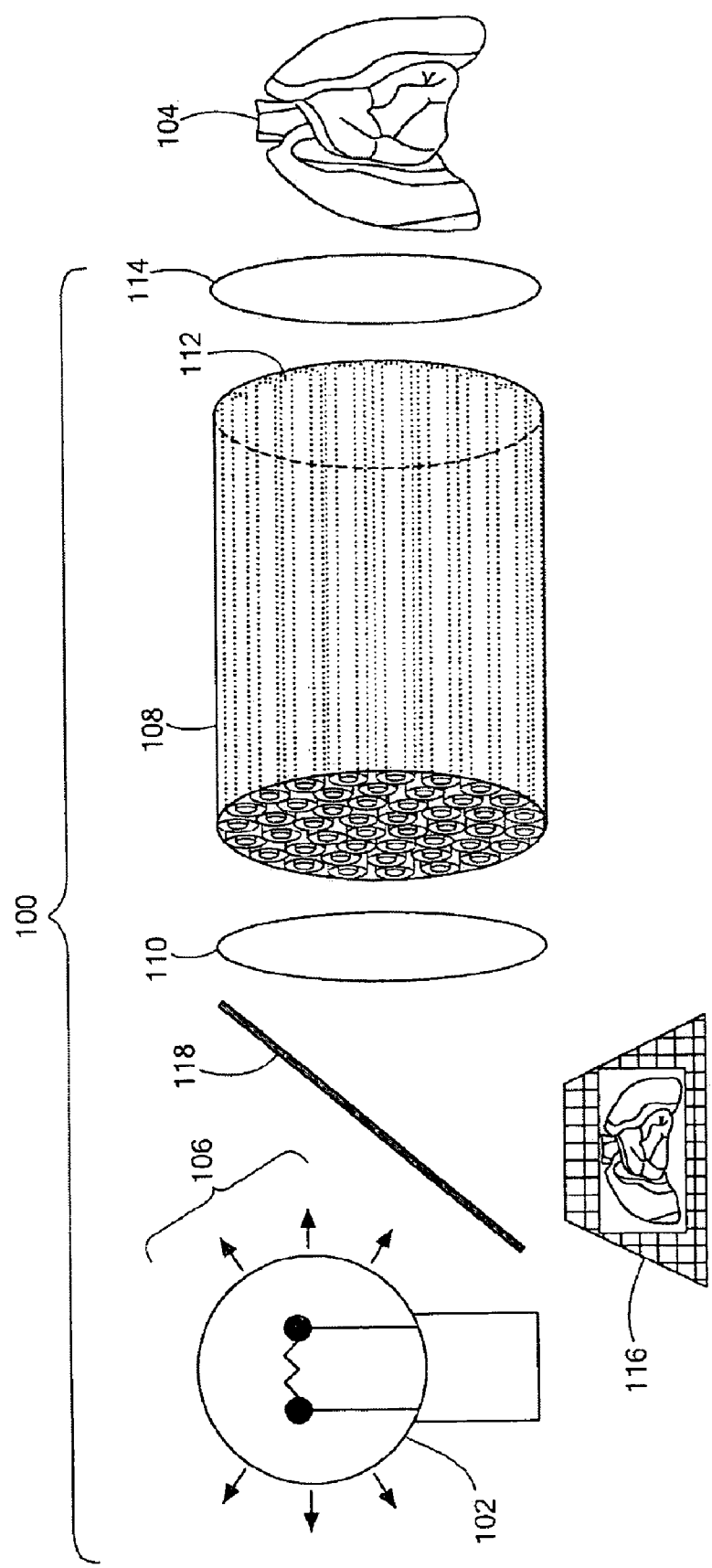
FIG. 1 is a schematic depiction of a typical prior art coherent fiber bundle endoscope.

In accordance with preferred embodiments of the invention, various techniques are provided for overcoming the aforesaid problems with fiber bundles in order to achieve coherence imaging through these bundles. These techniques are simple and inexpensive to implement, and result in an instrument that can acquire 3-D structure of internal tissues at micron-scale resolutions in a fraction of a second. This method is suitable for integration with existing visible light imaging instruments, and even simplifies existing instrumentation, thereby advantageously reducing cost.

Coherence microscopy, which includes, but is not limited to optical coherence microscopy (OCM) and optical coherence tomography (OCT), uses broadband illumination to peer beneath surfaces that can only be superficially observed with visible light microscopy. It does so, typically, by using near infrared light, although the present invention is not limited with respect to spectral range. Near-infrared light typically penetrates biological tissues further than visible light. OCM uses the coherence gating of the light to determine the depth of tissue layers from which scattering arises.

Unfortunately, the coherent fiber bundle, which has been so successful for visible microscopy of internal organs, has not been adapted successfully to coherence microscopy. Coherence microscopy typically imposes requirements that are not met by the fibers in a typical coherent fiber bundle. Attempts to use fiber bundles for coherence microscopy have resulted in severely distorted images that are unusable for practical clinical use. Present designs of coherence microscopy instruments are unable to tolerate the flaws introduced into the optical image introduced by typical fiber bundles.

While single-mode fiber bundles might be compatible with coherence microscopy, they are not used, in the current art, because they would compromise the performance of the bundle for visible microscopy due to coupling loss into the small cores of single mode fiber, and due to the small filling factor of the cross-section of each fiber constituted by the core.

Moreover, single-mode fiber bundles for application in coherence microscopy would require a development effort obviated by the adaptation of existing fiber bundles to coherence microscopy in accordance with the present invention.

In the following discussion, distortions introduced into the image by coherent fiber bundles are reviewed, and instrument innovations that can advantageously reduce or eliminate the artifacts caused by these distortions are detailed. These innovations are compatible with present visible-light microscopy systems, thereby advantageously facilitating combined visible/coherence fiber-bundle microscopy systems which are readily achievable, and which also constitute an aspect of the present invention. Additional advantages of the invention described herein are that the scattered signal is conveyed through all of the fibers simultaneously, coupled into all of the fibers simultaneously and collected from all of the fibers simultaneously, thereby greatly enhancing the signal gathering capacity of the instrument because an entire area of the object can be illuminated at once. Distortions due to signal propagation through a fiber bundle are now reviewed in the context of their effect on the received signal.

1. Phase distortion. The time delay for a light signal to travel through a fiber is not constant, but is very sensitive to changes in the mechanical strain on the fiber (e.g. twisting, bending, and stretching) and the temperature of the fiber. Variations in the delay of tens of femtoseconds per meter of fiber are not uncommon. Even sub-femtosecond fluctuations in the delay can corrupt phase measurements, which are used in frequency-domain scanning to infer object structure and Doppler imaging to infer object motion. This distortion is present in catheter-based OCT imaging which uses a single optical fiber, but is exacerbated when a fiber bundle is used.
2. Multimode distortion. The fibers used in fiber bundles are typically multimode fibers which are unsuitable for OCT, which uses single-mode fibers. In single-mode fibers, the signal conforms to a single spatial mode in the fiber which travels down the fiber at a nearly uniform speed. However, several spatial modes can propagate in multimode fibers, typically at several different speeds. As a result, a signal coupled into a multimode fiber typically divides over many modes, and the copies of the signal in each mode travel at different speeds down the fiber. As a result, several overlapping copies of the signal arrive at the end of the fiber at different times. The multimode distortion can introduce ghost artifacts into the image that are due to the overlapping of several copies of the signal, not unlike the ghost artifacts encountered on broadcast television.
3. Crosstalk distortion. Because the cores in a fiber bundle are so close together, light coupling can occur between the cores. Guided modes in fibers, as in any dielectric guide, typically have exponentially decaying evanescent "tails" outside of the cores, so that the mode is not completely confined to the core, but extends somewhat outside of it. If the cores are placed close enough together, the mode tail of one core will overlap with an adjacent core, causing the mode to leak into the nearby core. This will cause ghost images to appear in nearby adjacent axial scans. Cores in fiber bundles for visible-light microscopy are usually placed close together to maximize the area available for light collection, and the slight amount of crosstalk is tolerated. However, crosstalk signals will coherently interfere when laser light is used, so that the crosstalk produces a much larger distortion to coherent light than the incoherent light used in visible-light microscopy.

In general, the foregoing distortions do not cause significant problems for visible light microscopy because it typically uses highly incoherent illumination and detection. In visible light microscopy, the signal carried in each fiber is mutually spatially incoherent, so that crosstalk signals between different fibers do not interfere. Because incoherent detection is used, only the total power in the received light signal is recorded, which is not sensitive to fluctuations in time delay on the order of picoseconds or femtoseconds caused by phase distortion and multimode distortion. The insensitivity to these problems is a direct consequence that the illumination and detection are incoherent processes.

In accordance with embodiments of the invention, coherence imaging is adapted to allow incoherent illumination and detection.

Figure 2:
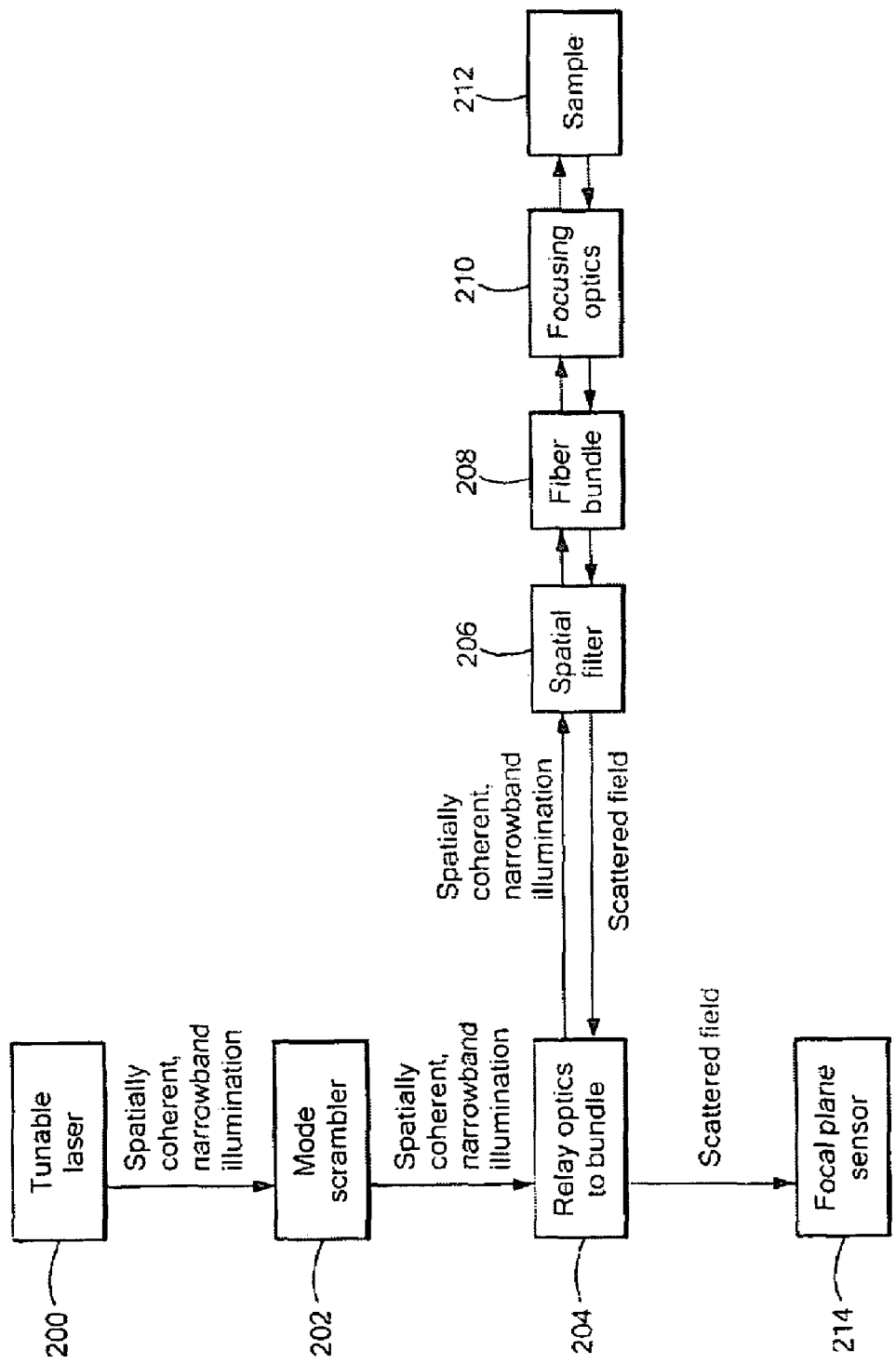
FIG. 2 is a block diagram depicting coherence microscopy performed in accordance with embodiments of the present invention.

One embodiment of the invention is now described with reference to the block diagram of FIG. 2. The overall operation of the instrument is as follows. The illumination is produced by a tunable laser 200 which produces spatially coherent light of a narrow bandwidth that can be tuned over a wide range of frequencies. This light is scrambled by a mode scrambler 202 to make the light spatially incoherent but still narrowband. The relay optics 204 convey the light to a spatial filter 206 and, after the spatial filter, the fiber bundle 208. The light emerges from the fibers in the bundle and is focused by a lens 210 into the sample 212. Light scattered back from the sample is refocused into the fiber bundle by the focusing optics. The light emerges from the bundle, is filtered by the spatial filter again, and then conveyed back through the relay optics to the focal plane sensor 214, where the intensity of the field is detected and recorded.

The illumination source is a tunable laser which produces a single spatial mode beam in a very narrow bandwidth for a given frequency setting. In accordance with preferred embodiments of the invention, a titanium-sapphire laser is employed, typically tuned over a portion, 680-830 nm, of its spectral range. The frequency of the laser can be tuned over a large bandwidth, with larger bandwidths achieving improved axial resolution. Lasers with a single spatial mode produce spatially coherent light. At a given tuned frequency, the tunable laser must have a bandwidth that achieves a coherence length longer than twice the distance from the reference surface to the furthest depth into the object of interest. This way, interference can occur between the signals scattered from the reference surface and the signal scattered from the largest depth of interest. If the largest depth of interest in the object is $\Delta l$ distant from the reference surface, and the refractive index of the medium is n, then the bandwidth $\Delta f < c/2n\Delta l$, where c is the speed of light. In addition, the error in center frequency for tuning the laser must also be less than $\Delta f$ to ensure that the frequency error does not distort features at depths of $\Delta l$ or greater inside the sample For example, with a typical tissue depth of $\Delta l = 2$ mm, and a typical tissue refractive index of $n=1.4$, the maximum bandwidth and maximum tuning error of the laser $\Delta f$ must be less than 53.5 GHz.

Figure 3:
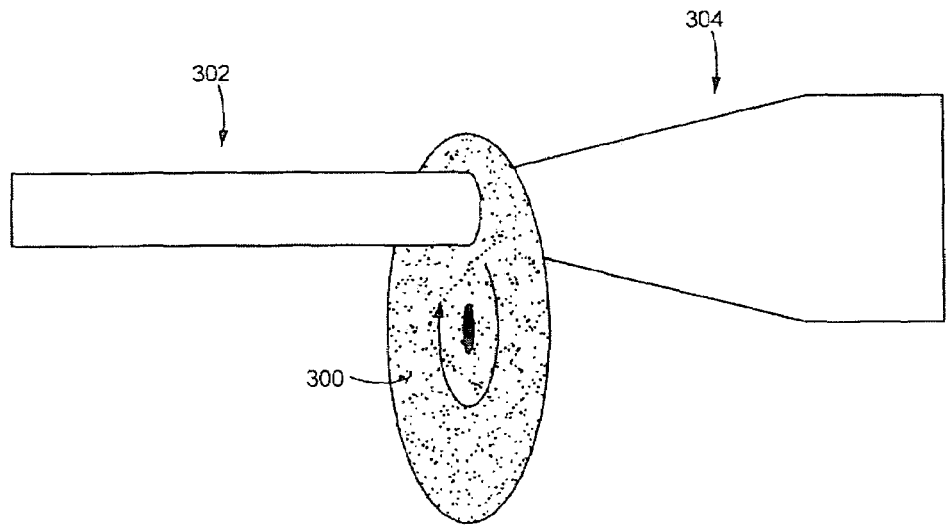
FIG. 3 shows an embodiment of a mode scrambler for use in accordance with an embodiment of the present invention.

A mode scrambler makes the light incoherent so as to decorrelate the light signals coupled into various fibers of the fiber bundle. This prevents interference between the signals contained in different fibers in the bundle, thereby minimizing crosstalk interference. The mode scrambler applies a random phase and/or amplitude to various points on a wavefront to decorrelate the signals at the different points on the wavefront. By using a mode scrambler, spatially incoherent light may be obtained despite the narrow spectral bandwidth of a source. Such light is very useful when quasi-monochromatic, spatially incoherent, radiation is needed. There are many ways to build a mode scrambler, all within the scope of the present invention. One method of mode scrambling, described with reference to FIG. 3, uses a translated diffusing optic 300 such as a roughened glass plate that is spun or moved across the wavefront of beam 302. The thickness of a roughened glass plate will vary randomly on the scale of the wavelength of the light. Because the phase of the light will be modified by the thickness of the plate, a random phase can be applied at various points on the wavefront by using a diffusing plate. By spinning or translating the plate, the phase at various points on the wavefront can be randomized over time such that emergent beam 304 is spatially incoherent. Other ways to build mode scramblers are to use spatial light modulators (e.g. acousto-optic, electro-optic, micromirror array, or liquid crystal) with randomly time varying phase and amplitude patterns applied to them.

After the mode of the laser is scrambled, the incoherent light is conveyed by relay optics to the entrance facet of the fiber bundle. The relay optics may be lenses or mirrors, forming a telescope. Preferably, the field is relayed both afocally and telecentrically, which is to say that collimated rays at either end are relayed as collimated rays at the other. The same relay optics may thus be used to relay the signal scattered backwards from the sample to the focal plane sensor, as shown in FIG. 2. The relay optics are preferably achromatic to the wavelength range over which the laser is employed.

Design of a suitable diffuser, as known in the art, requires selection of the scale over which the wavefront will be randomized (i.e. the speckle size). For a diffusing glass plate, the randomization scale is governed by the feature size of bumps or scratches that form the structures on the plate. The speckle size should be chosen so that after magnification/demagnification by the relay optics the speckle size is about the size of the core of a fiber in the fiber bundle. If the size is significantly smaller, light throughput may suffer, and if it is larger, the field will not be sufficiently spatially incoherent to eliminate the unwanted interference effects.

Another consideration is that, in accordance with a preferred embodiment of the invention, the phase is randomized on a timescale fast enough so that many hundreds or thousands of speckles are averaged over for each exposure interval on the focal plane sensor. Fortunately, by choosing a small speckle size and a high rotation rate (hundreds or thousands of revolutions per minute) for a diffusing glass plate, this is typically easily achieved.

Figure 4:
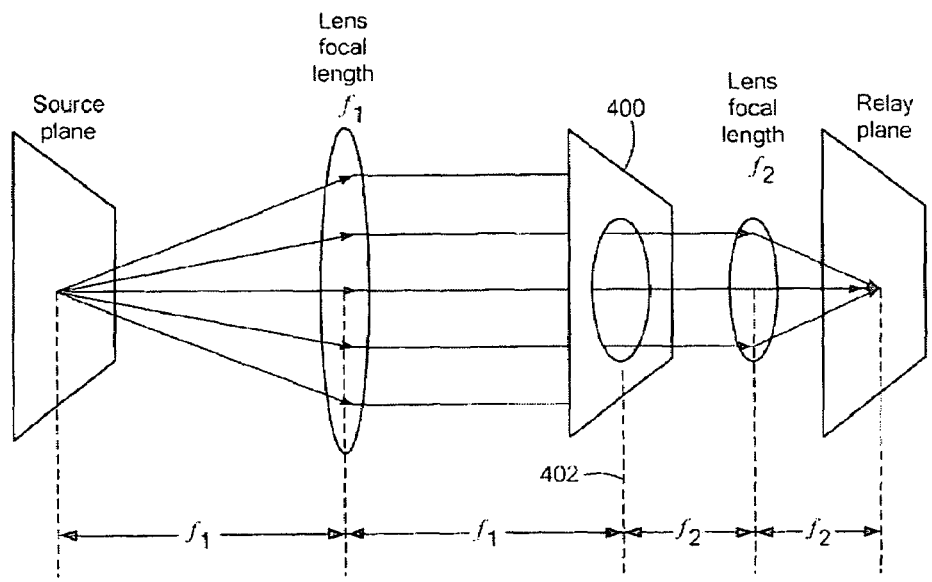
FIG. 4 shows an exemplary set of relay optics for use in accordance with an embodiment of the present invention.

As shown schematically in FIG. 4, a spatial filter (such as a pupil 400) may included in-line with the relay optics so as to spatially bandlimit the illumination field so that the speckle size is nearly the same as the size of the core of a fiber in the fiber bundle. The spatial filter also filters the light returning from the bundle. The spatial filter is employed to remove the light emerging from the bundle present in the higher order modes. These modes tend to consist of higher spatial frequencies, and so will be mostly removed using a low-pass spatial filter. This is one way that the multimode distortion can be minimized. The spatial filter helps bandlimit the fields so that the incoming incoherent illumination is largely coupled into the lowest order mode. The spatial filter also discards the higher order modes from the signal scattering back through the fiber bundle so it does not cause multimode interference. Thus, spatial filtering may advantageously serve to reduce the effect of multimode distortion.

A spatial filter can be implemented as a Fourier plane filter as detailed for example in *Introduction to Fourier Optics,* J. Goodman (3d ed., 2005), incorporated herein by reference. The Fourier plane filter is an example of a 1:1 magnification afocal and telecentric telescope. A circular pupil 400 is placed in the Fourier (or pupil) plane 402, with its size determining the bandlimit of the optical field. For convenience, instead of building a separate spatial filter, a pupil can be placed inside the relay optics at the pupil plane to effect the spatial filter, as shown in FIG. 4. This way, the relay optics and spatial filter can be integrated together to save space and cost.

The spatial bandlimit of the spatial filter should be chosen so that the point spread function width at the fiber entrance facet is approximately the core size of a fiber. This will best ensure that the speckle size of the illumination incoherent light is not too small, and also that the filter removes higher order modes emerging from the bundle while keeping the lowest order mode.

The fiber bundle consists of hundreds, or thousands, of optical fiber channels, from 10-100 microns in size, with cores from 5-90 microns in size. The fiber bundle is coherent in the sense that the fibers in the bundle remain parallel the entire length of the bundle without crossing or tangling. Each fiber in the bundle consists of a high refractive index core and a low refractive index cladding, and the light is guided inside the core by total internal reflection. In general, the individual fibers in the bundle are multimode, and temperature fluctuations and strains on the fiber cause random phase fluctuations in the fibers. Each of the fibers will conduct a mutually incoherent signal relayed to it by the relay optics. At the end of the fiber bundle the illumination signals emerge, and are imaged by the focusing optics into the sample. The illumination is backscattered by various layers in the sample, and the distance to the layers is conveyed in the time delay and/or phase of the return signal. This return signal is collected by the fiber bundle.

Demonstrations of OCT through a fiber bundle by Ford et al., *"Full-field optical coherence tomography using a fibre imaging bundle,"* Proc. SPIE, v. 6079, pp. H-1-9 (Feb. 20, 2006), and by Sarantavgas et al., *"Fizeau-based optical coherence tomography (OCT) using a fibre imaging bundle,"* Photonics and Imaging in Biology and Medicine II, (Sep. 5, 2006), have utilized time-domain interferometry rather than spectral scanning.

Figure 5:
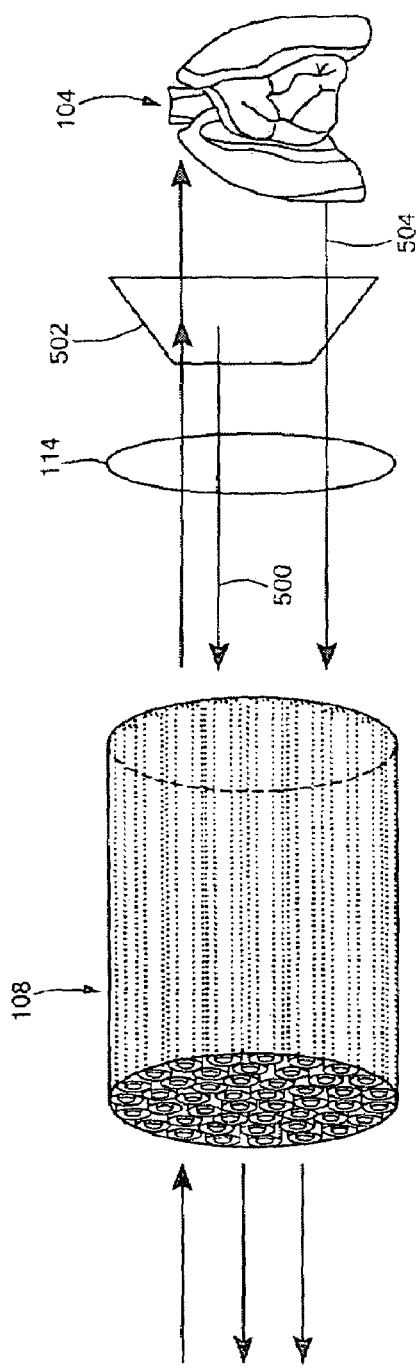
FIG. 5 shows a Fizeau interferometer for compensating, in accordance with embodiments of the present invention, phase distortions caused by motion of a sample.

Referring, now, to FIG. 5, the fiber bundle 108, focusing lens 114, and sample 104 typically form a Fizeau-type interferometer, as shown in FIG. 5, wherein a reference beam 500 is reflected from a surface 502 that is in the same optical path as the optical field 504 being sampled. This is in contrast to Michelson or Mach-Zehnder type interferometers where there are two separate paths for the reference and signal beams. Having two separate paths allows the maximum flexibility in altering the two reference and signal beams separately, but any phase fluctuations between the paths sensitively affects the phase of the detected interferogram. By using a common path for the interferometer, the phase fluctuations of the path are common to both the reference and sample signals and therefore cancel and minimally influence the phase of the interferogram.

One difficulty encountered in endoscopy is that the magnification of features may change as a function of distance from the focusing lens at the end of the bundle. As a result, it may be difficult to ascertain the size of a feature because its apparent size may depend sensitively on the distance of the probe to the features being imaged. Since feature size may have diagnostic value, it is desirable to minimize uncertainty in the scaling. Because coherence imaging already provides information about the distance to surfaces and features, this already assists in gauging the distance to features and therefore the scale. However, the focusing lens 114 can be designed to image the end of the fiber bundle 108 telecentrically into the sample to make the image approximately scale-invariant with range from the lens. This is a common strategy already used in machine vision inspection systems. The design of a miniature compound lens for telecentric imaging, for example, out of graded-index lenses or miniature achromatic lenses, is known within the art of optical design and fabrication and can be incorporated into the end of the fiber probe along with the reference surface. A telecentric lens can be as simple as two converging achromats arranged as a Keplerian telescope. A pupil stop can be incorporated into the lens system at the end of the fiber probe to spatially filter the light returning to the fiber bundle scattered from the sample. This spatial filter will ensure that the backscattered light is coupled primarily to the lowest-order mode if the pupil size is chosen to make the point spread function width on the fiber bundle facet approximately the core size of a fiber.

A Fizeau system is especially attractive for use with a fiber bundle because phase fluctuations are always occurring in the fibers. By reflecting a reference beam from a surface from the end of the fiber adjacent to the sample, the reference beam will inherently contain all of the same phase fluctuations as the signal beam scattered from the sample. In this design, we place a partially reflective surface either on the end of the fiber bundle, or preferably in contact with the sample at its top surface. A coating can be deposited on the end of the fiber bundle to reflect a small fraction of the light emerging from the fiber bundle back into the bundle. Alternatively, a glass window or microscope cover slip can be placed on top of the sample to provide the reference reflection. Placing the window in contact with the sample has the additional advantage that motions of the sample will be partially compensated because the phase fluctuation caused by motion of the sample will be cancelled by the common motion of the reference surface in contact with it. Interference between the reference reflection and the signal that is measured on the focal plane array (as the wavelength is scanned) contains the sample structure. The amount of power contained in the reflection should be 2 to 10 times the power being collected from the sample. Optical coatings and/or index matching materials and fluids can be used to control the magnitude of the reflection from the reference surface to produce the required ratio between reference and sample powers. Properly setting this ratio ensures that the dynamic range of the focal plane sensor can be well utilized. By using the Fizeau interferometer, the phase distortions can be compensated.

Since OCT based on spectral-domain scanning is sensitive to undesired reflections that may occur due to optical surfaces in this beam path, and since any reflection from a surface in close proximity to the sample can effectively act as a reference reflection, spurious images may be introduced between these extra reflections and the sample signal. To avoid this, optical coatings on surfaces, wedged surfaces, and index matching fluids inside the probe may be required to eliminate unwanted reflections and adjust the magnitude of the desired reference reflection.

A further benefit that can be realized using a Fizeau interferometer is that it can mitigate the polarization fading that often occurs in optical fiber interferometers. Twisting, bending, or stretching fibers can induce birefringence into the fibers so that the polarization of the signal is altered during propagation through the fiber. If separate reference and sample arms are used, the polarizations introduced into both signals may not be the same. Because orthogonal polarizations do not interfere, the mismatch of polarization between the reference and sample produces a reduction in the detected interference signal. As the fiber is moved, the polarization of the sample signal may change causing variations in the magnitude of the interference signal called polarization fading. However, by using a common path interferometer like the Fizeau interferometer, any random polarization changes introduced by the fiber will be common to the reference and sample signals and therefore the interference between the two is preserved. However, the polarization of the signal emerging from the fiber bundle may be random, even if the reference and signal share a common polarization state. Therefore, to minimize polarization fading, the optics in the beam path, e.g. beamsplitters and optical filters, for example, should be designed to conduct both polarizations equally, so that the randomly polarized signal is conveyed with minimal fluctuations as the polarization varies. Polarization-independent amplitude beamsplitters and filters are readily available from manufacturers such as Newport, Inc.

Figure 8:
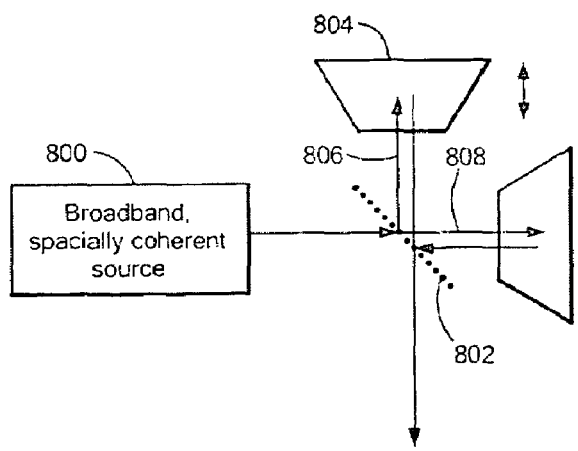
FIG. 8 is a diagram showing a source for a coherence imaging system, in accordance with alternative embodiments of the present invention, in which a broadband source is shown for time-domain scanning in place of the tunable source used for spectral-domain scanning.

We also note that it is not required to use spectral scanning in conjunction with the other methods of coherence imaging through the fiber bundle disclosed. By replacing the tunable laser shown in FIG. 2 with the source 800 shown in FIG. 8, one can scan the relative time delay between the reference and sample signals rather than the wavelength of the source. In FIG. 8, source 800 is a broadband laser such as a mode-locked Ti-sapphire laser, an amplified spontaneous emission source, or a superluminescent diode that emits all of the wavelengths in the desired bandwidth continuously. This source produces a collimated beam of broadband but spatially coherent light over the entire bandwidth of interest. This collimated beam is split into two parts 806, 808 with a beam splitter 802, and the two parts are delayed relative to each other using scanned mirrors 804 or other variable delay mechanism. The two parts are overlapped with a beam splitter, and then conducted to the mode scrambler of FIG. 2. The focal plane array will detect an interferogram that will measure the time-domain interferometric cross-correlation between the signal and reference signals returned from each fiber in the bundle as the delay is scanned. This interferogram will encode the magnitude of the scattering signal collected from various distances from the focus of each respective fiber in the bundle. For conventional coherence ranging, neglecting defocus effects, this signal can be interpreted as the 3-D volumetric scattering image of the sample.

Figure 6:
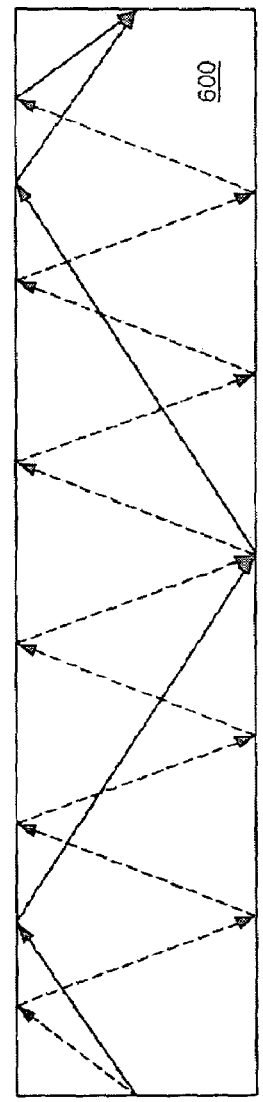
FIG. 6 illustrates the use of mode dispersion to prevent temporal overlap of energy propagated in respective modes of a waveguide, in accordance with embodiments of the present invention.

Another improvement to the fiber bundle may be made, in accordance with certain embodiments of the invention, to minimize multimode interference. Different modes of the fibers travel at different speeds. If the fiber is made long enough, the slower signals of the higher order modes will fall behind the faster signals of the lower order modes, and eventually will no longer overlap in time. Once they no longer overlap, interference does not occur between them. FIG. 6 depicts this effect for a slab waveguide 600 between conductors, but the principle is the same for a circular dielectric waveguide. The path of the lowest order mode is given by the solid line, while the next higher mode is given by the dotted line. Because the higher order mode must travel a longer distance to reach the end of the waveguide, it arrives later. If the waveguide is made long enough, the modes will arrive at the end of the waveguide far enough apart that they do not overlap in time and therefore will not interfere.

The minimum length of fiber needed to separate the two lowest order modes may be crudely estimated as $$l = \frac{2k^2 n^2 d^2 \Delta l}{3\pi^2},$$

where $k=2\pi/\lambda$ is the free-space wave number of the illumination frequency, where $\lambda$ is the wavelength, n is the refractive index of the core material, d is the diameter of the core, and $\Delta l$ is the total depth of the sample to scan. For typical values, $\lambda=1$ μm, n=1.5, d=10 μm, and $\Delta l=2$ mm, the minimum length l is 1.2 m. This is well within typical lengths of fiber bundles. Making the fiber bundle of sufficient length should help minimize multimode interference by preventing the signals in each mode from overlapping in time.

Another concern of using a multimode fiber is the possibility of coupling between modes inside the fiber bundle. It is possible that scattering processes (e.g. Rayleigh scattering or defects) inside the fiber may scatter signal between the lower-order mode and higher-order modes and vice-versa, so that spatial filtering exterior to the fiber may not remove the contributions of the higher-order modes that have scattered into the lowest-order mode. This problem, however, may also be mitigated. The equations that govern the propagation of light through a multimode optical fiber are the same form as the time-dependent Schrödinger equation of quantum mechanics. Therefore mathematical analyses of the time-dependent Schrödinger equation also can be applied to a propagation inside a multimode fiber. If one applies the quantum adiabatic theorem to the propagation of the light along a multimode fiber, one finds that as long as the propagation constants, or speeds (which correspond to the eigenvalues of the system), of the modes are sufficiently different along the entire length of the fiber, light entering the fiber in a particular mode will remain in that mode over the length of the fiber. This is true even if the fiber profile is slowly (adiabatically) changing (e.g. due to bending or stress) along the length of the fiber. Therefore to minimize coupling inside the fiber between modes, one should ideally design the individual fibers inside the fiber bundle to have as great a difference in propagation speed as possible between the lowest-order mode and other higher-order modes. The high numerical aperture fibers typically employed in imaging fiber bundles usually already satisfy this condition, especially if the core size is not too large, and therefore coupling inside the fiber between the lowest-order mode and higher-modes should already be minimal. However, the coupling can be minimized by designing the fibers to have a large difference in propagation speed between the lowest-order mode and the other modes, which can be achieved, among other methods, by increasing the index contrast between the core and cladding, and decreasing the core size. Because the visible light imaging capability of imaging fiber bundles is insensitive to the propagation speed in the fiber, such changes do not compromise the visible-light imaging performance of the bundle.

Finally, the field emerging from the fiber bundle, consisting of both the reference and sample signals, is relayed to the focal plane sensor, where the intensity of the field is detected and recorded. Typically the focal plane sensor is a CMOS array or a charge coupled device (CCD), but may be any detector which detects the intensity of the incoming field and digitizes into a data stream recorded by a digital computer. The frequency of the tunable laser source is scanned between a minimum and maximum frequency of interest, and at various frequencies the interferogram is recorded. By taking the inverse Fourier transform of the acquired interferograms with respect to the frequency, the three-dimensional structure of the sample is inferred. This is done in a manner similar to typical processing of OFDR (optical frequency domain reflectometry) data, except that the inverse Fourier transform is applied to the entire set of two-dimensional interferograms acquired by the focal plane sensor. The Fourier transform can be implemented numerically using the Fast Fourier Transform for example. If the frequency is sampled at non-uniform intervals, it may need to be resampled to a uniform spacing using an interpolator.

One complication that the fiber bundle introduces into the measured interferogram is that the field scattered from the sample is collected only at discrete areas defined by the positions of the cores of the fiber bundle. This introduces high spatial frequencies into the detected field that are not present in the field scattered by the sample. To compensate for this, higher spatial frequencies may be digitally low-pass filtered, in accordance with embodiments of the present invention, to remove them from the hologram measured on the sensor. A numerical Fourier Transform may be used for such filtering purposes, for example. If the fibers are arranged in the bundle on a rectangular grid with period D, spatial frequencies higher than ½D are introduced by the sampling effect of the discrete cores, and can be filtered out. The interferograms produced by other patterns of fibers such as regular hexagonal grids can also be filtered to remove aliasing effects. This filter not only reduces aliasing due to discrete fiber core sampling, but may also serve to reduce the amount of information needed to be stored and processed about each hologram.

The methods of interferometric synthetic aperture microscopy (ISAM), described in U.S. Provisional Patent Application Ser. No. 60/819,593, filed Jul. 10, 2006 and both appended hereto and incorporated herein by reference, may be applied to the data, and the diffraction of each illumination beam away from its respective focus may be accounted for. Because the data collected at each pixel is scattered from a beam that is made incoherent by the mode scrambler with respect to the other beams, the data at each pixel on the focal plane sensor can be treated as if each were collected from a single illumination beam that was scanned over the sample rather than many simultaneously illuminating beams. Therefore it can be treated in the same manner as serially scanned data once the aliasing due to the discrete sampling by fiber cores is removed.

Figure 7:
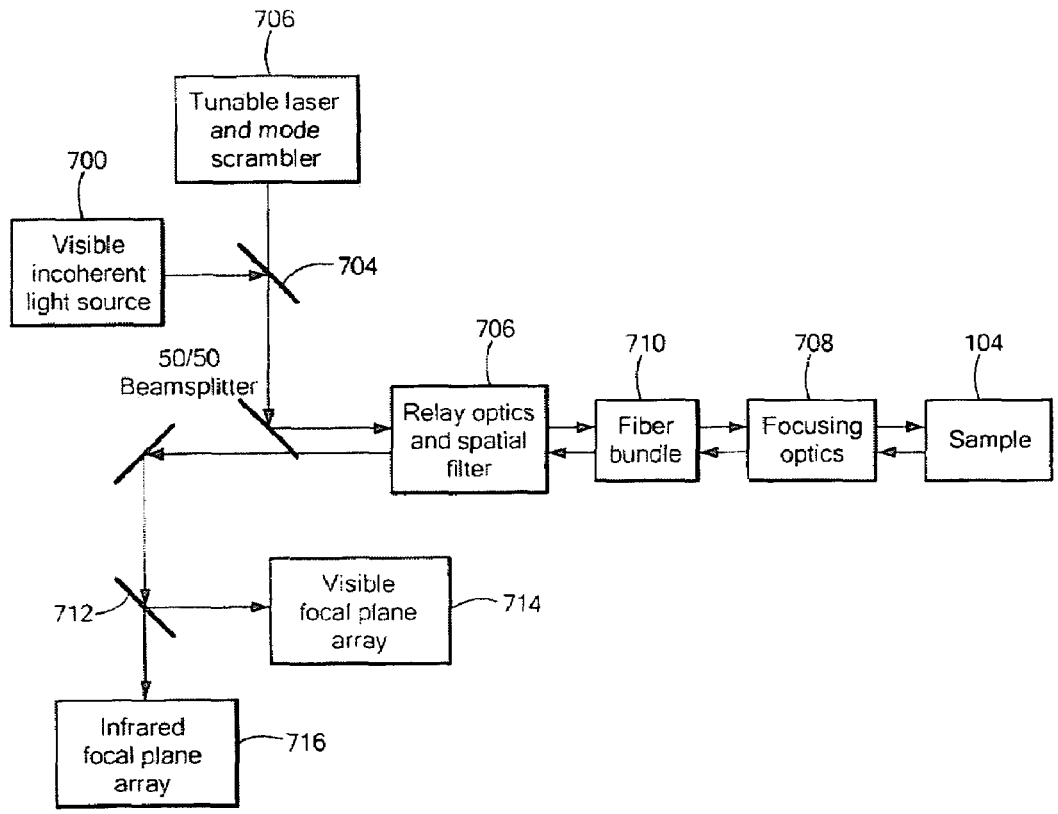
FIG. 7 is a block diagram of a joint imaging system for visible light microscopy and coherence microscopy sharing a common fiber bundle, in accordance with embodiments of the present invention.

Integrating coherence imaging with the visible light microscopy is straightforward, and an embodiment of an integrated system is shown schematically in FIG. 7. Separate light sources generate the incoherent light 700 needed for visible light microscopy (e.g. a halogen lamp), and a tunable laser and mode scrambler 702 can generate the infrared tunable spatially incoherent light. These can be combined by means of a dichroic beamsplitter 704. The relay optics 706 and focus optics 708 are adapted to image both the visible and infrared wavelength bands, and are preferably achromatized over the entire bandwidth to achieve satisfactory imaging quality. The light that returns from fiber bundle 710 is separated by a further dichroic beamsplitter 712, and the visible and infrared signals can be separately detected by respective visible 714 and infrared 716 focal plane arrays.

The embodiments of the invention heretofore described are intended to be merely exemplary and numerous variations and modifications will be apparent to those skilled in the art, including various combinations of four different methods that have been described. All such variations and modifications are intended to be within the scope of the present invention as defined in any appended claims.

What is claimed is:

1. A method for performing optical coherence microscopy, the method comprising:
   a. illuminating a sample with an instantaneously substantially monochromatic source of illuminating light via an optical fiber bundle, the illuminating light characterized by an instantaneous wavelength;
   b. reducing spatial coherence of the light prior to coupling the light into the fiber bundle;
   c. scanning the instantaneous wavelength of the illuminating light;
   d. collecting light scattered by features beneath the surface of the sample;
   e. coupling the scattered light into a distal end of the fiber bundle; and
   f. interfering the illuminating light and the scattered light to derive an image of the features beneath the surface.

2. A method as in claim 1, further comprising spatially filtering the light prior to coupling the light into the fiber bundle.

3. A method for performing optical coherence microscopy, the method comprising:
   a. illuminating a surface with a substantially monochromatic source of light via an optical fiber bundle, the substantially monochromatic source characterized by an instantaneous wavelength, wherein illuminating includes scanning the instantaneous wavelength of the illuminating light;
   b. spatially filtering the light prior to coupling the light into the fiber bundle;
   c. collecting light scattered by features beneath the surface of the sample;
   d. coupling the scattered light into a distal end of the fiber bundle; and
   e. interfering the illuminating light and the scattered light to derive an image of the features beneath the surface.

4. An apparatus for performing optical coherence microscopy, the apparatus comprising:
   a. an optical fiber bundle;
   b. a source of substantially spatially coherent light for illuminating a sample via the optical fiber bundle;
   c. a spatial filter interposed between the source of coherent light and the optical fiber bundle;
   d. exit optics for coupling light from the optical fiber bundle onto a surface of the sample and for collecting light scattered by features beneath the surface of the sample; and
   e. an interferometer for comparing the phase of light scattered by features beneath the surface of the sample with a reference derived from the identical source of substantially spatially coherent light.

5. An apparatus as in claim 4, wherein the source of substantially spatially coherent light includes a substantially monochromatic source characterized by an instantaneous wavelength varied over time.

6. An apparatus as in claim 4, wherein the source of substantially spatially coherent light includes a source of infrared light.

7. An apparatus as in claim 4, wherein the source of substantially spatially coherent light includes a source of near infrared light.

8. An apparatus as in claim 4, wherein the interferometer includes a Fizeau interferometer disposed substantially at the distal end of the fiber bundle.

9. An apparatus in accordance with claim 8, wherein the Fizeau interferometer includes an optical plate interposed between the distal end of the fiber bundle and the surface of the sample.

* * * * *